United States Patent
Kreft

(10) Patent No.: US 7,191,671 B2
(45) Date of Patent: Mar. 20, 2007

(54) PARTICULATE DEPOSIT AVOIDANCE AND PROBE POSITIONING

(75) Inventor: Norbert Kreft, Meerbusch (DE)

(73) Assignee: AVL North America Inc., Plymouth, MI (US)

( * ) Notice: Subject to any disclaimer, the term of this patent is extended or adjusted under 35 U.S.C. 154(b) by 186 days.

(21) Appl. No.: 10/978,209

(22) Filed: Oct. 29, 2004

(65) Prior Publication Data
US 2005/0109129 A1 May 26, 2005

Related U.S. Application Data

(60) Provisional application No. 60/515,733, filed on Oct. 30, 2003.

(51) Int. Cl.
*G01N 1/20* (2006.01)

(52) U.S. Cl. ................................ 73/863.81

(58) Field of Classification Search ............. 73/863.81, 73/23.31
See application file for complete search history.

(56) References Cited

U.S. PATENT DOCUMENTS

| | | | |
|---|---|---|---|
| 3,699,814 A | 10/1972 | Kaufman | |
| 4,228,676 A | 10/1980 | Myers | |
| 4,361,028 A | 11/1982 | Kamiya et al. | |
| 4,586,367 A | 5/1986 | Lewis | |
| 4,660,408 A | 4/1987 | Lewis | |
| 5,050,374 A * | 9/1991 | Hunter | 60/780 |
| 5,058,440 A | 10/1991 | Graze, Jr. | |
| 5,090,258 A * | 2/1992 | Yamasaki et al. | 73/863.03 |
| 5,109,708 A * | 5/1992 | Lawless | 73/863.11 |
| 5,410,907 A * | 5/1995 | Strom et al. | 73/23.31 |
| 6,928,890 B2 * | 8/2005 | Gehner et al. | 73/863 |
| 6,959,590 B2 * | 11/2005 | Hendren et al. | 73/118.1 |
| 7,044,009 B2 * | 5/2006 | Graze, Jr. | 73/863.03 |
| 7,059,205 B1 * | 6/2006 | Weaver | 73/863.03 |
| 2003/0136177 A1 | 7/2003 | Hendren et al. | |
| 2004/0107762 A1 | 6/2004 | Silvis et al. | |

FOREIGN PATENT DOCUMENTS

| | | | |
|---|---|---|---|
| DE | 4420193 A * | 6/1994 | |
| JP | 57-16333 | 1/1982 | |
| JP | 2004205253 A * | 7/2004 | |
| WO | WO 02/070116 A1 | 9/2002 | |

OTHER PUBLICATIONS

Mott Metallugical Corporation Brochure entitled, "Precision Porous Metal Filter Elements", published cira: 1989.
Sierra Instruments Brochure entitled, "Process Gas Mass Flow Controllers and Meters", published circa: 1988.
Paul M. Giever, Article In Advances in Instrumentation, vol. 29, Part 3, Paper No. 708, published:1974.

(Continued)

*Primary Examiner*—Hezron Williams
*Assistant Examiner*—John Fitzgerald
(74) *Attorney, Agent, or Firm*—Carlson, Gaskey & Olds

(57) ABSTRACT

A perforated mixing plate and is fluid passage are used in conjunction with a dilution tunnel to prevent particulate matter from collecting on the sampling system components. An inlet of a sampling probe is offset from the centerline of the dilution tunnel to a location corresponding to an average particulate matter concentration along a flow profile of a sample mixture to reduce the length of the dilution tunnel.

18 Claims, 2 Drawing Sheets

OTHER PUBLICATIONS

JJ Wu and R.C. Flagan entitled, "Onset of Runaway Nucleation in Aerosol Reactors", Journal of Applied Physics 61:1365-1371, published 1986.

P. Biswas, X, Li, and S.E. Pratsinis entitled, "Optical Waveguide Preform Fabrication: Silica Formation and Growth In a High Temperature Aerosol Reactor", Journal of Applied Physics 65: 2445-2450, published 1989.

Russell R. Graze, Jr. entitled,"Development of a Miniaturized, Dilution-Based Diesel Engine Particulate Sampling System for Gravimetric Measurement of Particulates", SAE Technical Paper Series from the 44th Annual Earthmoving Industry Conference Peoria, Illinois, Apr. 20 & 21, 1993. pp. 1-12.

Search Rpt. PCT/US2004/035972.

* cited by examiner

PARTICULATE DEPOSIT AVOIDANCE AND PROBE POSITIONING

BACKGROUND OF THE INVENTION

This application claims priority to provisional application Ser. No. 60/515,733 filed Oct. 30, 2003.

The invention relates to an exhaust sampling system having a dilution tunnel. Prior art exhaust sampling system using tunnels have two significant problems. First, particulate matter is deposited on portions of the dilution tunnel causing inaccuracies in the results since this particulate matter is never sampled or collected on the filter media and measured. Prior art dilution tunnels having mixing plates that are prone to stagnant areas in which the turbulent flow of exhaust and dilution gases through the orifice recirculate and collect on the surface of the mixing plate near the orifice. Particulate matter carried in the mixture is deposited on walls in the stagnant area, which results in this particulate matter not being collected by the filter resulting in inaccuracies. One proposed solution was to provide a fluid chamber arranged outside of the dilution tunnel. The dilution tunnel included perforations in its walls that permitted fluid to flow from the fluid chamber into the dilution tunnel. However, this arrangement did not prevent particulate matter from collecting on the surfaces of the dilution tunnel.

Second, prior art tunnels are significantly long and difficult to package. Prior art tunnels are designed to have a considerably long passage to ensure that the exhaust gas and dilution gas have adequately mixed by the time the mixture is sampled within the tunnel. Also, the length contributes to the amount of particulate matter that tends to collect on the surfaces of the dilution tunnel.

What is needed is a shorter dilution tunnel having which is configured in such a way to prevent the deposit of particulate matter on the surfaces of the dilution tunnel.

SUMMARY OF THE INVENTION

The present invention provides an exhaust sampling system for measuring particulate matter. The system includes an exhaust gas source and a dilution gas source. A dilution tunnel includes an upstream side in fluid communication with the exhaust gas and dilution sources. The exhaust gas source carries particulate matter. A mixing plate is arranged in the dilution tunnel and includes an orifice enhancing mixing of the exhaust gas and dilution sources to produce a sample mixture. Multiple perforations are arranged about the orifice to permit a flow through the mixing plate in addition to the flow through the orifice that prevents the particulate matter from collecting on the mixing plate.

The example system also includes a probe that is arranged in the dilution tunnel downstream from the mixing plate for receiving the sample mixture. The sampler includes a filter having a filter element for collecting particulate matter. An inlet of the probe is offset from a centerline of the dilution tunnel by a predetermined amount corresponding to an average particulate concentration location along a profile of the sample mixture to reduce the tunnel length.

The dilution tunnel includes an a wall spaced from the dilution tunnel providing a fluid passage, the fluid passage for carrying a fluid in a direction generally parallel with a flow direction of the sample mixture within the dilution tunnel to prevent particulate matter from collecting on the inner surface of the dilution tunnel.

Accordingly, the present invention provides a shorter dilution tunnel having which is configured in such a way to prevent the deposit of particulate matter on the surfaces of the dilution tunnel.

DETAILED DESCRIPTION OF THE INVENTION

Figure 1:
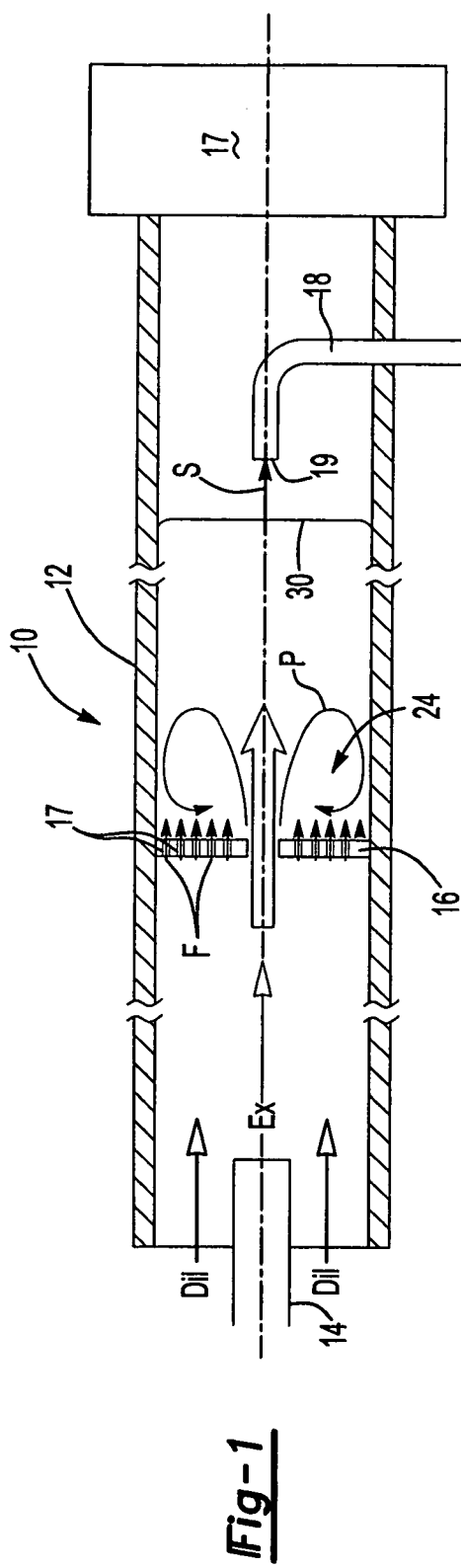
FIG. 1 is a cross-sectional view of the inventive dilution tunnel having a perforated mixing plate.

An inventive exhaust sampling system 10 is shown in FIG. 1. The system 10 includes a dilution tunnel 12 carrying exhaust gas from an exhaust source 14, such as a tailpipe of a vehicle. Dilution air is also present in the dilution tunnel 12 and is mixed with the exhaust gas by an orifice in a mixing plate 16. The dilution gas may be atmospheric air or another fluid. The exhaust gas and dilution gas mixes along the length of the dilution tunnel 12 to provide a sample mixture.

Once the gases are homogeneously mixed a sampling probe 18 having an inlet 19 samples a portion of the mixture for subsequent analysis. The sample S taken by the probe 18 may go through a filter 20, which traps particulate matter found in the sample S. A pump 22 is used to pull the sample through the sampling probe 18. A device 17 pulls the mixture through the dilution tunnel and may also include various flow measurement devices, transducers, and other components found in exhaust sampling system. The system 10 is highly schematic and is only intended to be exemplary.

There is typically a stagnant area 24 downstream of the mixing plate 16 where particulate matter tends to collect. This particulate matter does not get collected by the filter 20, which results in inaccuracies. The inventive mixing plate 16 utilizes numerous perforations 17 or holes in the mixing plate 16 permitting a flow F to pass through the wall of the mixing plate 16. The flow F is sufficient to prevent particulate matter from being deposited on the mixing plate 16 and in the stagnant area 24 so that this particulate matter may be collected by the filter 20.

Prior art dilution tunnels typically position the probe 18 such that the inlet 19 is aligned with the centerline of the dilution tunnel 12. Furthermore, the probe inlet 19 is positioned at a point in which the concentration profile 30 of the mixture is uniform along the diameter of the dilution tunnel 12, which results in a very long dilution tunnel that is difficult to package within a test cell.

Figure 2:
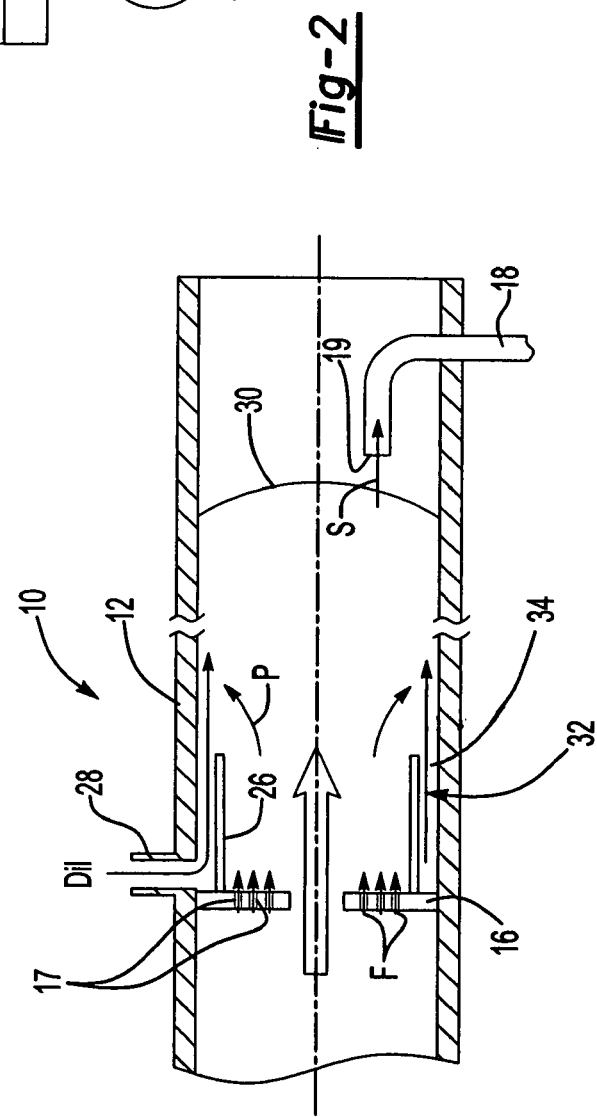
FIG. 2 is a cross-sectional view of an inventive dilution tunnel having a sampling probe offset from the centerline of the tunnel.

Referring to FIG. 2, particulate matter P from the mixture of exhaust and dilution gases once it has passed through the orifice of the mixing plate 16 tends to collect on the walls of the dilution tunnel 12, which results in the particulate matter P not being collected by the probe 18. As a compliment to the perforated mixing plate 16, the dilution tunnel 12 also includes an annular inner wall 26 spaced from the wall of the dilution tunnel 12. The wall 26 and dilution tunnel 12 provide an annular cavity 32 having an annular exit 34, in the example shown. The annular cavity 32 is arranged inwardly of the dilution tunnel and runs generally parallel with an inner surface 36 of the dilution tunnel. The cavity 32 and exit 34 are configured in such a way so as to encourage fluid flow along, or generally parallel with the inner surface 36, to prevent particulate matter from collecting along the inner surface 36.

A dilution source is connected at a fitting 28 to the space defined between the wall of the dilution tunnel 12 and the inner wall 26 so that dilution gas flows along the inner surface of the dilution 12, preventing particulate matter from collecting on the surface which would not be collected by the filter 20. The dilution source fluidly connected to the fitting may be the same as or different than the dilution source provided upstream of the mixing plate 16.

In another aspect of the this invention, the inlet 19 of the probe 18 may be positioned closer to the mixing plate 16 thereby shortening the length of the dilution tunnel 12. The concentration profile 30 of the mixture is not uniform along the dilution tunnel diameter at the location as the probe inlet 19 is positioned closer to the mixing plate 16. However, a radial location of the dilution inlet 19 may be selected such that the sample S represents an average.

Figure 3:
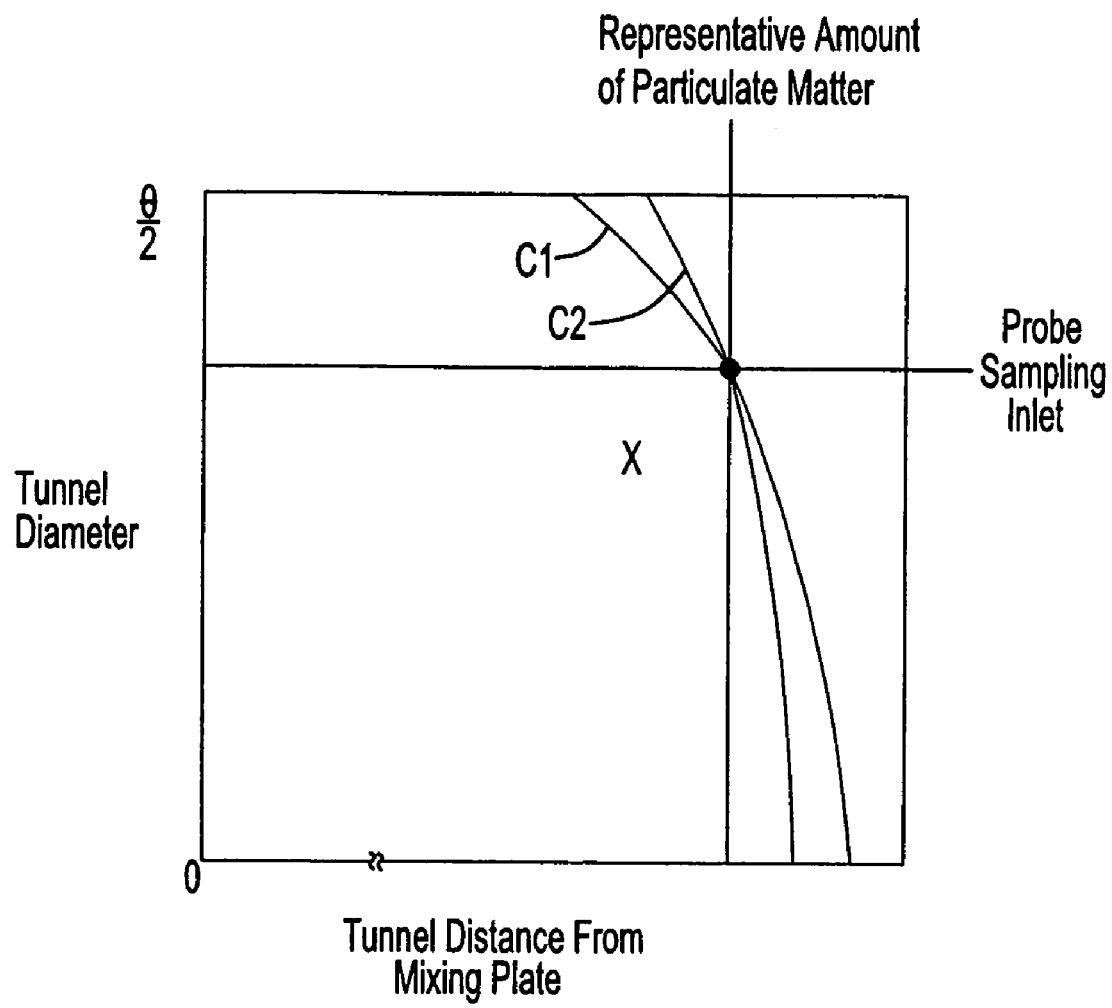
FIG. 3 is a graphical depiction of the offset probe sampling inlet relative to particulate matter concentration profiles.

Referring to FIGS. 2 and 3, the concentration profile 30 depicts a high concentration of a particulate matter near the centerline of the dilution tunnel and a low concentration of particulate matter near the walls of the dilution tunnel 12. Prior art arrangements using probes that are offset from the centerline are always positioned in an area having a uniform distribution of particulate matter across the diameter of the dilution tunnel. Since the sample taken by the probe 18 and collected by the filter 20 represents an integration of the particulate matter over the duration of the test, an average particulate concentration may be sampled. In FIG. 3, the sampling inlet is represented by location X. A representative amount of particulate matter may be collected at the position X for various concentration profiles. A first concentration profile C1 is representative of the distribution of particulate matter at a point in time during a particular test procedure. A second concentration profile C2 is also shown. The position X is selected such that the representative amount of particulate matter is collected accurately for various concentration profiles throughout the test procedure. The position X may be selected using fluid modeling software and/or empirically.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. An exhaust sampling system for measuring particulate matter comprising:
    an exhaust gas source and a dilution gas source;
    a dilution tunnel having an upstream side in fluid communication with the exhaust gas and dilution sources, the exhaust gas source having particulate matter; and
    a mixing plate arranged in the dilution tunnel and having an orifice enhancing mixing of the exhaust gas and dilution sources to produce a sample mixture, and multiple perforations arranged about the orifice, the perforations permitting a flow through the mixing plate in addition to the flow through the orifice that prevents the particulate matter from collecting on the mixing plate.

2. The system according to claim 1, wherein the mixing plate is arranged downstream from the exhaust gas source.

3. The system according to claim 1, wherein the dilution tunnel includes an a wall spaced from the dilution tunnel providing a fluid passage, the fluid passage for carrying a fluid in a direction generally parallel with a flow direction of the sample mixture within the dilution tunnel.

4. The system according to claim 3, wherein the wall is arranged radially inboard of the dilution tunnel.

5. The system according to claim 3, wherein the fluid passage is generally annular and including an exit arranged between the dilution tunnel and the wall.

6. The system according to claim 5, wherein the exit is bounded by the dilution tunnel and wall, the exit being generally annular.

7. The system according to claim 1, comprising a sampler including a probe that is arranged in the dilution tunnel downstream from the mixing plate, the probe receiving the sample mixture.

8. The system according to claim 7, wherein the sampler includes a filter having a filter element for collecting particulate matter.

9. The system according to claim 7, wherein the dilution tunnel includes a centerline, and the probe includes an inlet that is offset from the centerline by a predetermined amount corresponding to an average particulate concentration location along a profile of the sample mixture.

10. An exhaust sampling system for measuring particulate matter comprising:
    an exhaust gas source and a dilution gas source;
    a dilution tunnel having an upstream side in fluid communication with the exhaust gas and dilution sources, the exhaust gas source having particulate matter;
    a wall spaced from the dilution tunnel providing a fluid passage, the fluid passage providing a fluid along an inner surface of the dilution tunnel, and an exit providing the fluid in a flow direction generally parallel with the inner surface; and
    a mixing plate arranged in the dilution tunnel and having an orifice enhancing mixing of gases from the exhaust gas and dilution sources to produce a sample mixture.

11. The system according to claim 10, wherein the wall is arranged radially inboard of the dilution tunnel.

12. The system according to claim 10, wherein the fluid passage is generally annular and the exit is arranged between the dilution tunnel and the wall.

13. The system according to claim 12, wherein the exit is bounded by the dilution tunnel and wall, the exit being generally annular.

14. The system according to claim 10, wherein the wall adjoins the mixing plate on a downstream side.

15. The system according to claim 14, wherein the wall is arranged radially outward from the orifice.

16. The system according to claim 15, wherein the mixing plate includes perforations arranged between the orifice and the wall.

17. An exhaust sampling system for measuring particulate matter comprising:
    an exhaust gas source and a dilution gas source;
    a dilution tunnel in fluid communication with the exhaust gas and dilution sources, the exhaust gas source having particulate matter; and
    a wall spaced radially inwardly from the dilution tunnel providing a fluid passage, the fluid passage providing a fluid along an inner surface of the dilution tunnel, and an exit providing the fluid in a flow direction generally parallel with the inner surface, the wall arranged downstream from the exhaust gas source.

18. The system according to claim 17, comprising a sampler including a probe arranged in the dilution tunnel downstream from the wall, the probe receiving a sample mixture of gases from the exhaust gas and dilution sources, the dilution tunnel including a centerline, and the probe includes an inlet that is offset from the centerline by a predetermined amount corresponding to an average particulate concentration location along a profile of the sample mixture.

* * * * *